US008608967B2

(12) United States Patent
Miller et al.

(10) Patent No.: US 8,608,967 B2
(45) Date of Patent: Dec. 17, 2013

(54) MULTIPLE STATIONARY PHASE MATRIX AND USES THEREOF

(75) Inventors: Grover Miller, Little Rock, AR (US);
Drew R. Jones, Little Rock, AR (US);
Gunnar Boysen, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 73 days.

(21) Appl. No.: 13/039,950

(22) Filed: Mar. 3, 2011

(65) Prior Publication Data

US 2012/0226054 A1    Sep. 6, 2012

(51) Int. Cl.
*B01D 15/08* (2006.01)
(52) U.S. Cl.
USPC ......................................................... 210/656
(58) Field of Classification Search
USPC ......................................................... 210/656
See application file for complete search history.

(56) References Cited

U.S. PATENT DOCUMENTS

| 8,309,709 B2* | 11/2012 | Berg et al. ................ 536/124 |
| 2006/0020022 A1* | 1/2006 | Chekal et al. ............. 514/456 |
| 2011/0217539 A1* | 9/2011 | Bonner et al. ............. 428/314.2 |

OTHER PUBLICATIONS

Sreedhar et al. Journal of Chromatography A, 2008, 1215, 122-144.*
Louw et al. Journal of Chromatography A, 2008, 1208, 90-94.*
Erni et al. Journal of Chromatography A, 1978, 149, 561-569.*
Jandera et al. Journal of Separation Science—J Sep Sci , vol. 31, No. 9, pp. 1421-1437, 2008.*
Mack et al. Chromatographia (1988), 26, 197-205.*
Diaz-Perez et al. Chirality (1994), 6(4), 283-5.*
Wikoff et al., "Metabolomics analysis reveals large effects of gut microflora on mammalian blood metabolites", Proceedings of the National Academy of Sciences, 2009, pp. 3698-3703, vol. 106, No. 10.
Barreiro et al., "A column-switching method for quantification of the enantiomers of omeprazole in native matrices of waste and estuarine water samples", Talanta, 2010, pp. 384-391, vol. 82.
Bastani et al., "Determination of 8-epi PGF2a concentrations as a biomarker of oxidative stress using triple-stage liquid chromatography/tandem mass spectrometry", Rapid Communications in Mass Spectrometry, 2009, pp. 2885-2890, vol. 23.

Cabooter et al., "Kinetic plot method as a tool to design coupled column systems producing 100,000 theoretical plates in the shortest possible time", Journal of Chromatography A, 2008, pp. 23-34, vol. 1212.
Cabooter et al., "Investigation of the validity of the kinetic plot method to predict the performance of coupled column systems operated at very high pressures under different thermal conditions", Journal of Chromatography A, 2009, pp. 3895-3903, vol. 1216.
Caccamese et al., "Direct High-Performance Liquid Chromatographic Separation of the Enantiomers of Venlafaxine and 11 Analogs Using Amylose-Derived Chiral Stationary Phases", Chirality, 2009, pp. 569-577, vol. 21.
Chauveau-Duriot et al., "Simultaneous quantification of carotenoids, retinol, and tocopherols in forages, bovine plasma, and milk: validation of a novel UPLC method", Analytical and Bioanalytical Chemistry, 2010, pp. 777-790, vol. 397.
Herrero et al., "Serial coupled columns reversed-phase separations in high-performance liquid chromatography, Tool for analysis of complex real samples", Journal of Chromatography A, 2008, pp. 208-215, vol. 1188.
Louw et al., "Serial coupling of reversed-phase and hydrophilic interaction liquid chromatography to broaden the elution window for the analysis of pharmaceutical compounds", Journal of Chromatography A, 2008, pp. 90-94, vol. 1208.
Schettgen et al., "Fast determination of urinary S-phenylmercapturic acid (S-PMA) and S-benzylmercapturic acid (S-BMA) by column-switching liquid chromatography-tandem mass spectrometry", Journal of Chromatography B, 2008, pp. 283-292, vol. 863.
Schettgen et al., "A method for the quantification of biomarkers of exposure to acrylonitrile and 1,3-butadiene in human urine by column-switching liquid chromatography-tandem mass spectrometry", Analytical and Bioanalytical Chemistry, 2009, pp. 969-981, vol. 393.
Skov et al., "Handling within run retention time shifts in two-dimensional chromatography data using shift correction and modeling", Journal of Chromatography A, 2009, pp. 4020-4029, vol. 1216.
Sreedhar et al., "Preparative separation of multi-component mixtures using stationary phase gradients", Journal of Chromatography A, 2008, pp. 133-144, vol. 1215.
Stringham et al., "Memory Effect of Diethylamine Mobile Phase Additive on Chiral Separations on Polysaccharide Stationary Phases", Chirality, 2004, pp. 493-498, vol. 16.
Wang et al., "Increased Throughput and Reduced Carryover of Mass Spectrometry-Based Proteomics Using a High-Efficiency Nonsplit Nanoflow Parallel Dual-Column Capillary HPLC System", Journal of Proteome Research, 2008, pp. 2743-2755, vol. 7, No. 7.

* cited by examiner

*Primary Examiner* — Nizal Chandrakumar
(74) *Attorney, Agent, or Firm* — Polsinelli PC (57) ABSTRACT

The present invention generally provides a separation matrix comprising at least two stationary phases and a stationary phase comprising at least one chiral modality and at least one achiral modality. Also provided are methods of using the separation matrix or the stationary phase to separate enantiomers of one or more chiral molecules.

9 Claims, 8 Drawing Sheets

MULTIPLE STATIONARY PHASE MATRIX AND USES THEREOF

FIELD OF THE INVENTION

The present invention generally relates to separation materials and methods. In particular, it relates to separation matrices and/or stationary phases that are able to separate molecules on the basis of more than one type of interaction.

BACKGROUND OF THE INVENTION

Separation techniques are widely used in the biological, chemical, and pharmaceutical industries. Most separation technologies rely on one type of interaction between a molecule of interest and a stationary phase comprising a functional modality. For example, the molecule of interest and the functional modality of the stationary may interact via hydrophobic interactions, aromatic interactions, hydrophilic interactions, cation exchange interactions, anion exchange interactions, or stereoechemical interactions.

Enantiomers of a chiral compound differ only in the spatial arrangement of atoms around a chiral center. Enantiomers often act differently from each other in the chiral environment of a living organism. For example, enantiomers may have different pharmacological and toxicological effects and different pharmacokinetic properties. Many of the top selling pharmaceutically active agents are chiral compounds and many are provided as single enantiomers (e.g., Lipitor, Zocor, Plavix, and Nexium). Enantiomers of pharmaceutically active agents may be prepared either by asymmetric synthesis or the separation of racemic mixtures into single enantiomers using a chiral based separation technique. Typically, adequate resolution of the two enantiomers of a chiral compound is only achieved through the use of other types of separation technologies in combination with the chiral based separation technology. As such, the separation and isolation of a single enantiomer may be an expensive and time-consuming undertaking.

What is needed, therefore, is a single separation technology that utilizes several different separation principles. In particular, what is needed is a separation material that separates molecules on the basis of more than one type of interaction.

SUMMARY OF THE INVENTION

Briefly, therefore, one aspect of the present disclosure provides a separation matrix comprising at least two stationary phases.

Another aspect of the disclosure encompasses a stationary phase comprising at least one chiral modality and at least one achiral modality.

Still another aspect of the present disclosure provides a method for enantioseparation of at least one chiral molecule. The method comprises contacting a mixture comprising one or more chiral molecules with a matrix comprising at least one chiral stationary phase and at least one achiral stationary phase such that enantiomers of the one or more chiral molecules are separated.

A further aspect of the disclosure encompasses a method for enantioseparation of at least one chiral molecule. The method comprises contacting a mixture comprising one or more chiral molecules with a stationary phase comprising at least one chiral modality and at least one achiral modality such that enantiomers of the one or more chiral molecules are separated.

Other features and iterations of the disclosure are described in more detail below.

BRIEF DESCRIPTION OF THE FIGURES

FIG. 2 depicts representative extracted ion chromatograms of standards (100 nM) with three different column systems. For each column, the flow rate was 300 μL/min with 45% methanol and 55% $H_2O$ with 0.01% formic acid. Hydroxywarfarin standards were separated using a C18 column (top), a UPLC phenyl column (middle) and both the phenyl and chirobiotic columns in-series together (bottom). The extracted ion chromatograms specific for 10-hydroxywarfarin are shown separately (right). The insets symbolize the various system configurations with either one column or both in-series. Numbers indicate sites of hydroxylation while R or S signifies stereochemistry e.g. 7=7-hydroxywarfarin; S7=S-7-hydroxywarfarin. 10-Hydroxywarfarin contains two stereo-centers such that four configurations are possible (RR, RS, SR, SS). However, only stereochemistry at carbon 9 could be assigned, therefore peaks were given an "a" or "b" designation based on elution order e.g. R10a=10-hydroxywarfarin with R stereochemistry at carbon 9 and unknown stereochemistry at carbon 10.

DETAILED DESCRIPTION OF THE INVENTION

The present disclosure provides compositions and methods for resolving complex mixtures of molecules. Molecules of interest may be resolved by a variety of separation techniques. Typically, separation techniques resolve molecules of interest by contacting a mobile phase comprising the molecules of interest (e.g., solutes or volatiles) with a stationary phase comprising a functional modality, wherein the solutes or volatiles in the mobile phase have differing affinities with the functional modality of the stationary phase, and thus, separate. Traditionally, separation techniques utilize a stationary phase comprising one type of functional modality, such that the molecules of interest are separated on the basis of one type of interaction (e.g., hydrophobicity, charge, chiral recognition, etc.). Although various types of separation techniques may be used sequentially to separate complex mixtures or resolve closely related molecules, such techniques (e.g., two-dimensional chromatography) tend to be cumbersome and time-consuming. The applicants of the present disclosure have advantageously discovered that separation materials comprising multiple stationary phases or multiple functional modalities are able to quickly resolve complex mixtures of molecules.

Accordingly, the present disclosure provides a separation matrix comprising at least two stationary phases. Also provided herein is a stationary phase comprising at least one chiral modality and at least one achiral modality. The present disclosure also provides methods for separating the enantiomers of chiral molecules.

(I) Separation Matrix Comprising Multiple Stationary Phases

One aspect of the present disclosure is the provision of a separation matrix comprising at least two stationary phases. The separation matrix may comprise any combination of chiral and/or achiral stationary phases. The achiral stationary phase may be polar, nonpolar, hydrophilic, hydrophobic, reverse phase, normal phase, anionic, cationic, or combinations thereof. Accordingly, the separation phase disclosed herein is able to separate complex mixtures of molecules on the basis of several different types of interactions.

(a) Chiral Stationary Phases

The separation matrix of the invention may comprise at least one chiral stationary phase. A chiral stationary phase comprises an appropriate chiral selector. A chiral selector is the chiral component of the stationary phase that is capable of interacting enantioselectively with the enantiomers to be separated. Interaction of the chiral selector of the stationary phase with the enantiomers to be separated results in the formation of two labile diastereomers. These diastereomers differ in their thermodynamic stability, provided that at least three active points of the chiral selector participate in the interaction with corresponding sites of the enantiomers. Types of interactions between the chiral selector of the chiral stationary phase and each enantiomer include H-bonding, π-π interactions, dipole stacking, inclusion complexing, and steric bulk interactions. As a consequence of these interactions, one of the enantiomers forms more stable associations with the chiral selector and is more strongly retained with the chiral stationary phase than the other enantiomer. Non-limiting examples of suitable chiral selectors include macrocyclic glycopeptides, cyclodextrins, polysaccharide polymers, small molecules, and proteins.

In one embodiment, the chiral selector of the chiral stationary phase may be a macrocyclic glycopeptide. Macrocyclic glycopeptides are naturally occurring antibiotics produced by microorganisms. A macrocyclic glycopeptide comprises an aglycone "basket" made up of fused macrocyclic rings and a peptide chain with differing numbers of pendant sugar moieties. Chiral stationary phases comprising macrocyclic glycopeptides are available under the trade name Astec CHIROBIOTIC® (available from Sigma-Aldrich, Co. St. Louis, Mo.). Non-limiting examples of suitable macrocyclic glycopeptides include vancomycin (V, V2), ristocetin (R), teicoplanin (T, T2), and teicoplanin aglycone (TAG). In one preferred embodiment, the chiral stationary phase may comprise vancomycin V or vancomycin V2 as the chiral selector.

In another embodiment, the chiral selector of the chiral stationary phase may be a cyclodextrin. Cyclodextrins are cyclic oligosaccharides comprising D-glucose units connected through the 1 and 4 positions by a glycosidic linkages. The overall shape of a cyclodextrin is that of a truncated cone with an open cavity. The exterior of the cone is hydrophilic due to the presence of hydroxyl groups and the interior of the cavity is less hydrophilic than the aqueous environment, allowing for hydrophobic interactions. Cyclodextrins may have from 6 glucose units to 12 glucose units. Preferred cyclodextrins include a cyclodextrin (with 6 glucose units), β cyclodextrin, (with 7 glucose units), and γ cyclodextrin (with 8 glucose units). The hydroxyl groups on the rim of the cyclodextrin may be derivatized to include a variety of groups such as, for example, acetyl, alkyl (e.g., methyl, ethyl), hydroxyalkyl (e.g., hydroxyethyl, hydroxypropyl), hydroxypropylether, carboxymethyl, amino, methylamine, alkylammonium, butylammonium, heptakis, carbamate, naphthylether carbamate, 3,5-diphenyl carbamate, sulfobutylether, sulphate, phosphate, and so forth.

In a further embodiment, the chiral selector of the chiral stationary phase may be a polysaccharide polymer. The polysaccharide polymer typically comprises cellulose or amylose. The cellulose or amylose polymer may be derivatized to include a group such as arylcarbamate, phenylcarbamate, methylphenylcarbamate, dimethylphenylcarbamate, benzoate, methylbenzoate, acetyl, halo, chloro, and combinations thereof.

In still another embodiment, the chiral selector of the chiral stationary phase may be a small chiral molecule. Chiral stationary phases of this type are known as Pirkle type or brush-type phases. A Pirkle type phase may be a methyl ester of N-3,5-dinitrobenzoyl amino acids (e.g., Whelk-O 1, Whelk-O 2). Additional Pirkle type phases include derivatives of 3,5-dinitrobenzoyl propanoate, naphthylleucine, and a β-lactam structure. Additional chiral small molecules include proline derivatized with an alkyne moiety, quinine, quinine carbamates, crown ethers, chiral dicarboxylic acids, chiral calixarenes, and so forth.

In yet another embodiment, chiral selector of the chiral stationary phase may be a protein. In general, proteins have large numbers of chiral centers that may interact with enantiomers of a chiral molecule, provided the chiral molecule has an ionizable group such an amine or acid. Accordingly, any protein may be used as a chiral selector. Non-limiting examples of suitable proteins that may be used as chiral selectors include bovine serum albumin, human serum albumin, a-glycoprotein, and cellobiohydrase.

(b) Achiral Stationary Phases

The separation matrix of the invention may comprise at least one achiral stationary phase. The achiral stationary phase may be polar, nonpolar, hydrophilic, hydrophobic, reverse phase, normal phase, anionic, cationic, or combinations thereof. Thus, the achiral stationary phase may allow reverse phase interactions, hydrophobic interactions (HIC), hydrophilic interaction (HILIC), anion exchange interactions, cation exchange interactions, etc. Accordingly, the achiral stationary phase may comprise a functional group chosen from as alkyl, alkenyl, alkynyl, aryl, alkylaryl, alkylamide, alkylamino, alkyldiol, alkylcarboxy, alkylsulfonic, amide, amine, cyano, diol, carboxy, sulfonic, and the like. Preferred alkyl groups include those with 4, 6, 8, or 18 carbon atoms (e.g., C4, C6, C8, and C18). A preferred aryl group is phenyl. Suitable phenyl groups include e phenyl, biphenyl, fluorophenyl, fluorophenyl alkyl, etc. Preferred alkylphenyl groups include C3 phenyl, C4 phenyl, C6 phenyl, and C8 phenyl.

(c) Properties of the Stationary Phases

Each stationary phase may be a solid or a liquid. In general, each stationary phase is affixed to a solid support. For example, a stationary phase may be covalently bonded to the surface of a solid support. Such a stationary phase may be called a bonded stationary phase. Alternatively, a stationary phase may be coated onto the surface of a solid support. Such a stationary phase may be called a coated stationary phase. Lastly, a stationary phase may be immobilized on the surface of a solid support. Such a stationary phase may be called an immobilized stationary phase.

The stationary phase may be affixed to a variety of solid supports. The solid support may comprise an inorganic material, an organic polymeric material, or an inorganic-organic hybrid material. Non-limiting examples of suitable inorganic materials include silica, silica gel, silica-based materials, silicon, silicon oxide, structured silicon, modified silicon, alumina, zirconia, zeolite, aluminum oxides, titanium oxides, zirconium oxides, glass, modified glass, functionalized glass, and metals such as stainless steel, aluminum, gold, platinum, titanium, and the like. The organic polymer may be a natural polymer, a synthetic polymer, a semi-synthetic polymer, a copolymer, or combinations thereof. Non-limiting examples of suitable polymers include agarose, cellulose, divinylbenzene, methacrylate, methylmethacrylate, methyl cellulose, nitrocellulose, polyacrylic, polyacrylamide, polyacrylonitrile, polyamide, polyether, polyester, polyethylene, polystyrene, polysulfone, polyvinyl chloride, polyvinylidene. Non-limiting examples of suitable copolymers include acrylonitrile-divinylbenzene copolymers, polystyrene-divinylbenzene copolymers (e.g., chloromethylated styrene-divinylbenzene copolymer or sulphonated styrene-divinylbenzene copolymer), methacrylate-divinylbenzene copolymers, and polyvinyl chloride-divinylbenzene copolymers. An inorganic-organic hybrid material may comprise an inner inorganic core and an organic polymeric coat surrounding the core. Suitable inorganic and organic polymeric materials are detailed above. In one exemplary embodiment, the solid support material may comprise silica or silica gel. In another exemplary embodiment, the solid support material may comprise an inorganic-organic hybrid material (e.g., a silica particle coated with a polymer, a bridged ethyl hybrid particle, and the like).

In some embodiments, the solid support may comprise a plurality of particles. As used herein, the term "particle" encompasses particles, spheres, beads, grains, and granules. The plurality of particles may have an average diameter ranging from about 0.5 micron to about 15 microns. In various embodiments, the average diameter of the plurality of particles may be about 1.5 microns, about 1.7 microns, about 1.8 microns, about 1.9 microns, about 2 microns, about 2.2 microns, about 2.5 microns, about 2.7 microns, about 3 microns, about 4 microns, about 5 microns, about 6 microns, about 8 microns, or about 10 microns. In a preferred embodiment, the average diameter of the plurality of particles may range from about 1.5 microns to about 5 microns.

The plurality of particles may be solid, porous, or superficially porous. In cases in which the plurality of particles are porous or superficially porous, the average pore size may range from about 25 angstroms to about 500 angstroms. In certain embodiments, the average pore size may be about 60 angstroms, about 80 angstroms about 100 angstroms, about 120 angstroms, about 150 angstroms, about 180 angstroms, about 200 angstroms, about 250 angstroms, about 300 angstroms, or about 400 angstroms. In a preferred embodiment, the average pore size may range from about 50 angstroms to about 200 angstroms.

In other embodiments, the solid support may be a three-dimensional structure such as a column, a tube, a capillary tube, etc. such that the stationary phase may be affixed to a surface of the structure. For example, the stationary phase may be affixed to the inner surface of the column, tube, or capillary tube. In other embodiments, the solid support may be a two-dimensional structure such as a slide, a membrane, a fiber, or a well, wherein the stationary phase may be affixed to a surface of the structure.

In general, the solid support comprising the stationary phase may be stable and retain function at a pressure ranging from about 15 megapascal (MPa) to about 200 MPa. In some instances, the pressure may be about 20 MPa, about 40 MPa, about 60 MPa, about 80 MPa, about 100 MPa, about 120 MPa, about 140 MPa, or about 160 MPa. Additionally, the solid support comprising the stationary phase may be stable and retain function at a temperature ranging from about −20° C. to about 200° C. In certain embodiments, the temperature may be about 20° C., about 30° C., about 40° C., about 50° C., about 60° C., about 70° C., about 80° C., about 90° C., or about 100° C.

(d) Applications

The separation matrix disclosed herein may be used to separate molecules of interest. Accordingly, the separation matrix may be used in a variety of separation techniques. Suitable separation techniques include, but are not limited to, high performance liquid chromatography (HPLC), ultra high performance liquid chromatography (UHPLC), high pressure HPLC, ultra fast HPLC, supercritical fluid chromatography (SFC), simulated moving bed (SMB) chromatography, gas chromatography (GC), ion chromatography (IC), counter current liquid chromatography (CCLC), capillary electrophoresis (CE), and capillary electrochromatography (CEC).

In some embodiments, for example, the separation matrix may be disposed within a chromatography column. The chromatography column may comprise at least two discrete zones, wherein each zone comprises one of the stationary phases. Alternatively, chromatography column may comprise a heterogeneous mixture of the two or more stationary phases.

The separation matrix may be used for many applications in biology, pharmaceuticals, medicine, and industry. For example, the separation matrix may be used to separate molecules of interest from complex mixtures of molecules. In particular, the separation matrix may be used to separate and isolate biologically active enantiomers of biological or pharmaceutical agents from inactive enantiomers of the agent.

(e) Preferred Embodiments

The separation matrix disclosed herein comprises at least two stationary phases. In one embodiment, the separation matrix comprises two different stationary phases. Table A lists non-limiting examples of embodiments in which the separation matrix comprises two different stationary phases.

TABLE A

| First Stationary Phase | Second Stationary Phase |
|---|---|
| Chiral | C8 |
| Chiral | C18 |
| Chiral | Phenyl |
| Chiral | Cyano |
| Chiral | Diol |
| Chiral | Anionic |
| Chiral | Cationic |
| C8 | C18 |
| C8 | Phenyl |
| C8 | Cyano |
| C8 | Diol |
| C8 | Anionic |
| C8 | Cationic |
| C18 | Phenyl |
| C18 | Cyano |
| C18 | Diol |
| C18 | Anionic |
| C18 | Cationic |
| Phenyl | Cyano |
| Phenyl | Diol |
| Phenyl | Anionic |
| Phenyl | Cationic |
| Cyano | Diol |
| Cyano | Anionic |
| Cyano | Cationic |
| Diol | Anionic |
| Diol | Cationic |
| Anionic | Cationic |

In another embodiment, the separation matrix may comprise three different stationary phases. For example, the separation matrix may comprise a chiral stationary phase, a C18 stationary phase, and a phenyl stationary phase. Alternatively, the separation matrix may comprise a chiral stationary phase, a phenyl stationary phase, and a cationic stationary phase. Those skilled in the art appreciate that many combinations are possible.

In a further embodiment, the separation matrix may comprise four different stationary phases. In yet another embodiment, the separation matrix may comprise more than four different stationary phases.

In exemplary embodiments, the separation matrix may comprise at least one chiral stationary phase and at least one achiral stationary phase. Table B lists various exemplary combinations in which the separation matrix comprises one chiral stationary phase and one achiral stationary phase.

TABLE B

| Chiral Stationary Phase | Achiral Stationary Phase |
|---|---|
| Macrocyclic glycopeptide | C8 |
| Macrocyclic glycopeptide | C18 |
| Macrocyclic glycopeptide | Phenyl |
| Macrocyclic glycopeptide | Cyano |
| Macrocyclic glycopeptide | Diol |
| Macrocyclic glycopeptide | Anionic |
| Macrocyclic glycopeptide | Cationic |
| Cyclodextrin | C8 |
| Cyclodextrin | C18 |
| Cyclodextrin | Phenyl |
| Cyclodextrin | Cyano |
| Cyclodextrin | Diol |
| Cyclodextrin | Anionic |
| Cyclodextrin | Cationic |
| Polysaccharide polymer | C8 |
| Polysaccharide polymer | C18 |
| Polysaccharide polymer | Phenyl |
| Polysaccharide polymer | Cyano |
| Polysaccharide polymer | Diol |
| Polysaccharide polymer | Anionic |
| Polysaccharide polymer | Cationic |
| Small chiral molecule | C8 |
| Small chiral molecule | C18 |
| Small chiral molecule | Phenyl |
| Small chiral molecule | Cyano |
| Small chiral molecule | Diol |
| Small chiral molecule | Anionic |
| Small chiral molecule | Cationic |
| Protein | C8 |
| Protein | C18 |
| Protein | Phenyl |
| Protein | Cyano |
| Protein | Diol |
| Protein | Anionic |
| Protein | Cationic |

(II) Stationary Phase Comprising Multiple Modalities

Another aspect of the present disclosure encompasses a stationary phase comprising at least one chiral modality and at least one achiral modality. Thus, the stationary phase disclosed herein is able to separate enantiomers on the basis of absolute stereo configuration as well as other physio-chemical interactions (e.g., hydrophobicity, hydrophilicity, charge, and so forth).

Chiral modalities are chiral selectors. Suitable examples of chiral selectors include macrocyclic glycopeptides, cyclodextrins, polysaccharide polymers, small molecules, and proteins, as detailed above in section (I)(a).

Suitable achiral modalities are functional groups that interact with the molecules of interest via hydrophobic, aromatic, reverse phase, hydrophilic, anion exchange, or cation exchange interactions. Examples of suitable functional groups are detailed above in section (I)(b).

The chiral and achiral modalities comprising the stationary phase may be affixed to a solid support. Examples of suitable solid supports and properties of the stationary phase are described above in section (I)(c).

The stationary phase comprising at least one chiral modality and at least one achiral modality may be used in a variety of separation techniques. Suitable separation techniques include, but are not limited to, high performance liquid chromatography (HPLC), ultra high performance liquid chromatography (UHPLC), high pressure HPLC, ultra fast HPLC, supercritical fluid chromatography, simulated moving bed chromatography, gas chromatography, ion chromatography, counter current liquid chromatography, capillary electrophoresis, and capillary electrochromatography.

In preferred embodiments, the stationary phase may comprise one chiral modality and at least one achiral modality. In one iteration, the stationary phase may comprise one chiral modality and one achiral modality. In other iteration, the stationary phase may comprise one chiral modality and two achiral modalities. In another iteration, the stationary phase may comprise one chiral modality and three achiral modalities. In still another iteration, the stationary phase may comprise two chiral modalities and at least one, two, three, or more than three achiral modalities. Table C presents examples of exemplary stationary phases.

TABLE C

| First Chiral Modality | First Achiral Modality | Second Achiral Modality |
|---|---|---|
| Macrocyclic glycopeptide | C8 | None |
| Macrocyclic glycopeptide | C18 | None |
| Macrocyclic glycopeptide | Phenyl | None |
| Macrocyclic glycopeptide | Cyano | None |
| Macrocyclic glycopeptide | Diol | None |
| Macrocyclic glycopeptide | Anionic | None |
| Macrocyclic glycopeptide | Cationic | None |
| Cyclodextrin | C8 | None |
| Cyclodextrin | C18 | None |
| Cyclodextrin | Phenyl | None |
| Cyclodextrin | Cyano | None |
| Cyclodextrin | Diol | None |
| Cyclodextrin | Anionic | None |
| Cyclodextrin | Cationic | None |
| Polysaccharide polymer | C8 | None |
| Polysaccharide polymer | C18 | None |
| Polysaccharide polymer | Phenyl | None |
| Polysaccharide polymer | Cyano | None |
| Polysaccharide polymer | Diol | None |
| Polysaccharide polymer | Anionic | None |
| Polysaccharide polymer | Cationic | None |
| Small chiral molecule | C8 | None |
| Small chiral molecule | C18 | None |
| Small chiral molecule | Phenyl | None |
| Small chiral molecule | Cyano | None |
| Small chiral molecule | Diol | None |
| Small chiral molecule | Anionic | None |
| Small chiral molecule | Cationic | None |
| Protein | C8 | None |
| Protein | C18 | None |
| Protein | Phenyl | None |
| Protein | Cyano | None |
| Protein | Diol | None |
| Protein | Anionic | None |
| Protein | Cationic | None |
| Macrocyclic glycopeptide | C8 | C18 |
| Macrocyclic glycopeptide | C8 | Phenyl |
| Macrocyclic glycopeptide | C8 | Cyano |
| Macrocyclic glycopeptide | C8 | Diol |
| Macrocyclic glycopeptide | C8 | Anionic |
| Macrocyclic glycopeptide | C8 | Cationic |
| Macrocyclic glycopeptide | C18 | Phenyl |
| Macrocyclic glycopeptide | C18 | Cyano |
| Macrocyclic glycopeptide | C18 | Diol |
| Macrocyclic glycopeptide | C18 | Anionic |
| Macrocyclic glycopeptide | C18 | Cationic |
| Macrocyclic glycopeptide | Phenyl | Cyano |
| Macrocyclic glycopeptide | Phenyl | Diol |
| Macrocyclic glycopeptide | Phenyl | Anionic |
| Macrocyclic glycopeptide | Phenyl | Cationic |
| Macrocyclic glycopeptide | Cyano | Diol |
| Macrocyclic glycopeptide | Cyano | Anionic |
| Macrocyclic glycopeptide | Cyano | Cationic |
| Macrocyclic glycopeptide | Diol | Anionic |
| Macrocyclic glycopeptide | Diol | Cationic |
| Macrocyclic glycopeptide | Anionic | Cationic |
| Cyclodextrin | C8 | C18 |
| Cyclodextrin | C8 | Phenyl |
| Cyclodextrin | C8 | Cyano |
| Cyclodextrin | C8 | Diol |
| Cyclodextrin | C8 | Anionic |
| Cyclodextrin | C8 | Cationic |
| Cyclodextrin | C18 | Phenyl |
| Cyclodextrin | C18 | Cyano |
| Cyclodextrin | C18 | Diol |
| Cyclodextrin | C18 | Anionic |

TABLE C-continued

| First Chiral Modality | First Achiral Modality | Second Achiral Modality |
|---|---|---|
| Cyclodextrin | C18 | Cationic |
| Cyclodextrin | Phenyl | Cyano |
| Cyclodextrin | Phenyl | Diol |
| Cyclodextrin | Phenyl | Anionic |
| Cyclodextrin | Phenyl | Cationic |
| Cyclodextrin | Cyano | Diol |
| Cyclodextrin | Cyano | Anionic |
| Cyclodextrin | Cyano | Cationic |
| Cyclodextrin | Anionic | Cationic |
| Cyclodextrin | Diol | Anionic |
| Cyclodextrin | Diol | Cationic |
| Polysaccharide polymer | C8 | C18 |
| Polysaccharide polymer | C8 | Phenyl |
| Polysaccharide polymer | C8 | Cyano |
| Polysaccharide polymer | C8 | Diol |
| Polysaccharide polymer | C8 | Anionic |
| Polysaccharide polymer | C8 | Cationic |
| Polysaccharide polymer | C18 | Phenyl |
| Polysaccharide polymer | C18 | Cyano |
| Polysaccharide polymer | C18 | Diol |
| Polysaccharide polymer | C18 | Anionic |
| Polysaccharide polymer | C18 | Cationic |
| Polysaccharide polymer | Phenyl | Cyano |
| Polysaccharide polymer | Phenyl | Diol |
| Polysaccharide polymer | Phenyl | Anionic |
| Polysaccharide polymer | Phenyl | Cationic |
| Polysaccharide polymer | Cyano | Diol |
| Polysaccharide polymer | Cyano | Anionic |
| Polysaccharide polymer | Cyano | Cationic |
| Polysaccharide polymer | Diol | Anionic |
| Polysaccharide polymer | Diol | Cationic |
| Polysaccharide polymer | Anionic | Cationic |
| Small chiral molecule | C8 | C18 |
| Small chiral molecule | C8 | Phenyl |
| Small chiral molecule | C8 | Cyano |
| Small chiral molecule | C8 | Diol |
| Small chiral molecule | C8 | Anionic |
| Small chiral molecule | C8 | Cationic |
| Small chiral molecule | C18 | Phenyl |
| Small chiral molecule | C18 | Cyano |
| Small chiral molecule | C18 | Diol |
| Small chiral molecule | C18 | Anionic |
| Small chiral molecule | C18 | Cationic |
| Small chiral molecule | Phenyl | Cyano |
| Small chiral molecule | Phenyl | Diol |
| Small chiral molecule | Phenyl | Anionic |
| Small chiral molecule | Phenyl | Cationic |
| Small chiral molecule | Cyano | Diol |
| Small chiral molecule | Cyano | Anionic |
| Small chiral molecule | Cyano | Cationic |
| Small chiral molecule | Diol | Anionic |
| Small chiral molecule | Diol | Cationic |
| Small chiral molecule | Anionic | Cationic |
| Protein | C8 | C18 |
| Protein | C8 | Phenyl |
| Protein | C8 | Cyano |
| Protein | C8 | Diol |
| Protein | C8 | Anionic |
| Protein | C8 | Cationic |
| Protein | C18 | Phenyl |
| Protein | C18 | Cyano |
| Protein | C18 | Diol |
| Protein | C18 | Anionic |
| Protein | C18 | Cationic |
| Protein | Phenyl | Cyano |
| Protein | Phenyl | Diol |
| Protein | Phenyl | Anionic |
| Protein | Phenyl | Cationic |
| Protein | Cyano | Diol |
| Protein | Cyano | Anionic |
| Protein | Cyano | Cationic |
| Protein | Diol | Anionic |
| Protein | Diol | Cationic |
| Protein | Anionic | Cationic |

(III) Methods for the Enantioseparation of Chiral Molecules

A further aspect of the present disclosure provides methods for separating enantiomers of at least one chiral molecule. In particular, enantiomers in complex mixtures of molecules may be separated because the separation matrix of the invention or the stationary phase of the invention are able to separate molecules on the basis of more than one type of interaction.

A first method comprises contacting a mixture comprising the chiral molecule(s) with a separation matrix comprising at least one chiral stationary phase and at least one achiral stationary phase such that enantiomers of the chiral molecule(s) are separated. Suitable examples of the separation matrix are detailed above in section (I), with exemplary embodiments presented above in Table B.

A second method comprises contacting a mixture comprising the chiral molecule(s) with a stationary phase comprising at least one chiral modality and at least one achiral modality such that enantiomers of the chiral molecule(s) are separated. Suitable examples of the stationary phase are detailed above in section (II). Exemplary embodiments are presented above in Table C.

The mixture used in the processes, i.e., the mixture comprising the chiral molecule(s), can and will vary. For example, the mixture may be a racemate, an organic synthesis reaction mixture, an extract of a biological synthesis reaction, a complex mixture of chiral and achiral molecules, and a biological sample comprising at least one chiral molecule. Suitable biological samples include plasma, serum, blood, urine, saliva, tears, lymph, intrauterine fluid, vaginal secretions, cerebrospinal fluid, intraventricular fluid, interstitial fluid, and the like.

The contacting step of the method may involve a separation technique such as high performance liquid chromatography (HPLC), ultra high performance liquid chromatography (UHPLC), high pressure HPLC, ultra fast HPLC, supercritical fluid chromatography, simulated moving bed chromatography, gas chromatography, ion chromatography, counter current liquid chromatography, capillary electrophoresis, and capillary electrochromatography. Those of skill in the art are familiar with the aforementioned techniques and are familiar with suitable detection methods, analysis methods, and/or data acquisition methods.

DEFINITIONS

To facilitate understanding of the invention, the following terms are defined.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups having at least one carbon-carbon double bond that preferably contain from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups having at least one carbon-carbon triple bond that preferably contain from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following example demonstrates one embodiment of the present disclosure.

Example 1

Novel Dual-Phase UHPLC/MS Assay for Profiling Enantiomeric Hydroxywarfarins and Warfarin in Human Plasma The following example was designed to test a prototype of a dual phase matrix. In particular, a reverse phase stationary matrix and a chiral stationary matrix were used sequentially without the use of additional pumps or switching mechanisms for the separation of enantiomers of warfarin and its metabolites.

(a) Materials and Methods

Reagents and Chemicals.

Racemic warfarin, racemic 4', 10, 6, 7, 8-hydroxywarfarins, and deuterated internal standards were obtained from Toronto Research Chemicals (Toronto, Canada). R-warfarin, S-warfarin, and 10-hydroxywarfarin were also obtained from Sigma-Aldrich (St. Louis, Mo.). Human plasma samples from patients receiving warfarin and blank plasma were purchased from BD Biosciences (San Jose, Calif.). Only age, sex, and concomitant drug information was provided for each of the samples.

Instrumentation and Conditions.

Hydroxywarfarin and warfarin analytes were quantified by dual-phase ultra high performance liquid chromatography tandem mass spectrometry (HPLC-MS/MS) utilizing two commercially available columns with distinctly different stationary phases. The first phase consisted of a phenyl-based reverse-phase chromatography using a Acquity HPLC BEH Phenyl column (2.1 mm×150 mm 1.7 µm particle column; Waters, Milford, Mass.), operated at 60° C. The second phase was chiral chromatography utilizing an Astec Chirobiotic V column (2.1 mm×150 mm, 5 µm; Supelco, Bellefonte, Pa.), operated at room temperature (21.6-22.4° C.). The flow rate of 300 μL/min was provided by an Acquity HPLC interfaced with a standard electro-spray ionization source to a Quantum Ultra triple quadrupole mass spectrometer. Warfarin, hydroxywarfarins, and deuterated internal standards were monitored in positive ion mode. Data were acquired in single reaction monitoring (SRM) mode using the ion transitions of 325 to 267 for 4"-hydroxywarfarin, 325 to 179 for 6, 7, and 8-hydroxywarfarin, 325 to 251 for 10-hydroxywarfarin, 309 to 163 for warfarin, 330 to 184 for d5-8-hydroxywarfarin, and 314 to 168 for d5-warfarin.

Plasma Extraction.

Human plasma samples were processed as described previously (Wikoff et al., Proc Natl Acad Sci, 2009, 106:3698). In brief, plasmas samples (50 μL) (blank, M61, M75, M76, and M80) were spiked with internal standards (10 μL, 60 μM d5-warfarin and 6 μM d5-8-hydroxywarfarin 50 mM potassium phosphate pH 7.4) and allowed to equilibrate for 12 hours at 4° C. Following equilibration, ice cold 0.2% formic acid in $H_2O$ (190 μL) was added to each sample, followed by ice cold 0.2% formic acid in acetonitrile (1000 μL). Samples were allowed to precipitate at 4° C. for 30 minutes, followed by centrifugation (10 min at 16,000 g) in a microcentrifuge. The supernatant (1000 μL) was then transferred to a new vial and dried down in a speed vacuum concentrator. Plasma extracts were resolubilized (40 μL) in mobile phase (55% methanol, 45% $H_2O$ with 0.01% formic acid) maintaining a 1:1 ratio with the original volume of plasma.

Microsomal Incubation with Warfarin Enantiomers.

Enantiomerically pure R-warfarin and 5-warfarin were metabolized by human liver microsomes pooled from 150 donors (HLM150 BD Biosciences) to generate R— or 5-hydroxywarfarin metabolites, respectively. Stock solutions of R-warfarin or 5-warfarin in ethanol were allowed to evaporate to dryness in a microfuge tube and were resolubilized in 50 mM potassium phosphate pH 7.4 for a final concentration of 25 μM or 500 μM in the reaction. The final concentration of microsomal protein was 2 mg/mL. The reaction was initiated by addition of NADPH, for a final concentration of 1 mM, and incubated at 37° C. The reaction was quenched at 30 min by addition of an equal volume of ice cold 0.4 M perchloric acid. The sample was centrifuged at 10,000 g for 10 min and the supernatant was transferred to a fresh vial for analysis by LC-MS/MS.

(b) Results

Characterization of Phenyl Column Chromatography.

Figure 2:
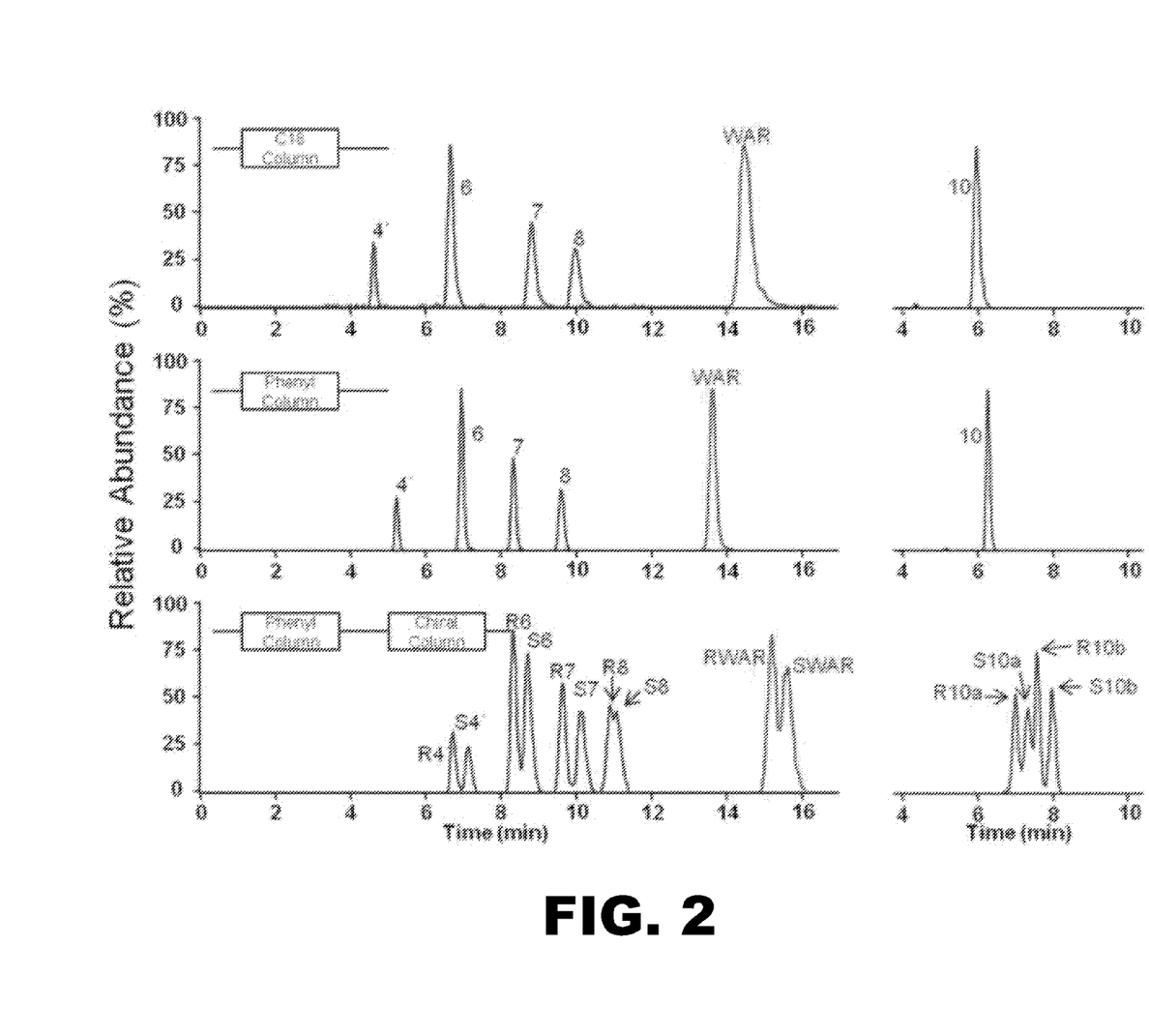

Initially, separation of hydroxywarfarins was explored using a variety of reverse-phase columns and isocratic conditions (data not shown). This evaluation demonstrated that the phenyl-based column achieved the highest efficiency and selectivity for separation of hydroxywarfarins (FIG. 2, middle). This is likely due to pi-stacking interactions between warfarin ring motifs and the phenyl group on the stationary phase. In comparison with the C18 column (BEH C18 column 2.1×150 mm, Waters), the peaks were approximately one half as wide at the base with the phenyl column and provided greater separation between 7 and 8-hydroxywarfarin (FIG. 2, top and middle). Varying the isocratic composition of methanol demonstrated that mobile phase compositions with less than 40% methanol resulted in long run times (>20 min) and unacceptably wide peaks. With isocratic compositions up to ~85% methanol, the phenyl column achieved baseline separation of all hydroxywarfarins. Sufficient separation of all hydroxywarfarins was achieved at 45% methanol with a peak resolution of 1 min between peaks at the same SRM transition (FIG. 2, middle). Operation at 60° C. significantly reduced the system pressure to ~8500 psi at a flow rate of 300 μL/min, while maintaining separation of all hydroxywarfarin metabolites. Although this method successfully separated mixtures of hydroxywarfarins into their regio-isomers, each peak represents a mixture of the R and S enantiomers.

Characterization of Chiral Column Chromatography.

Figure 3:
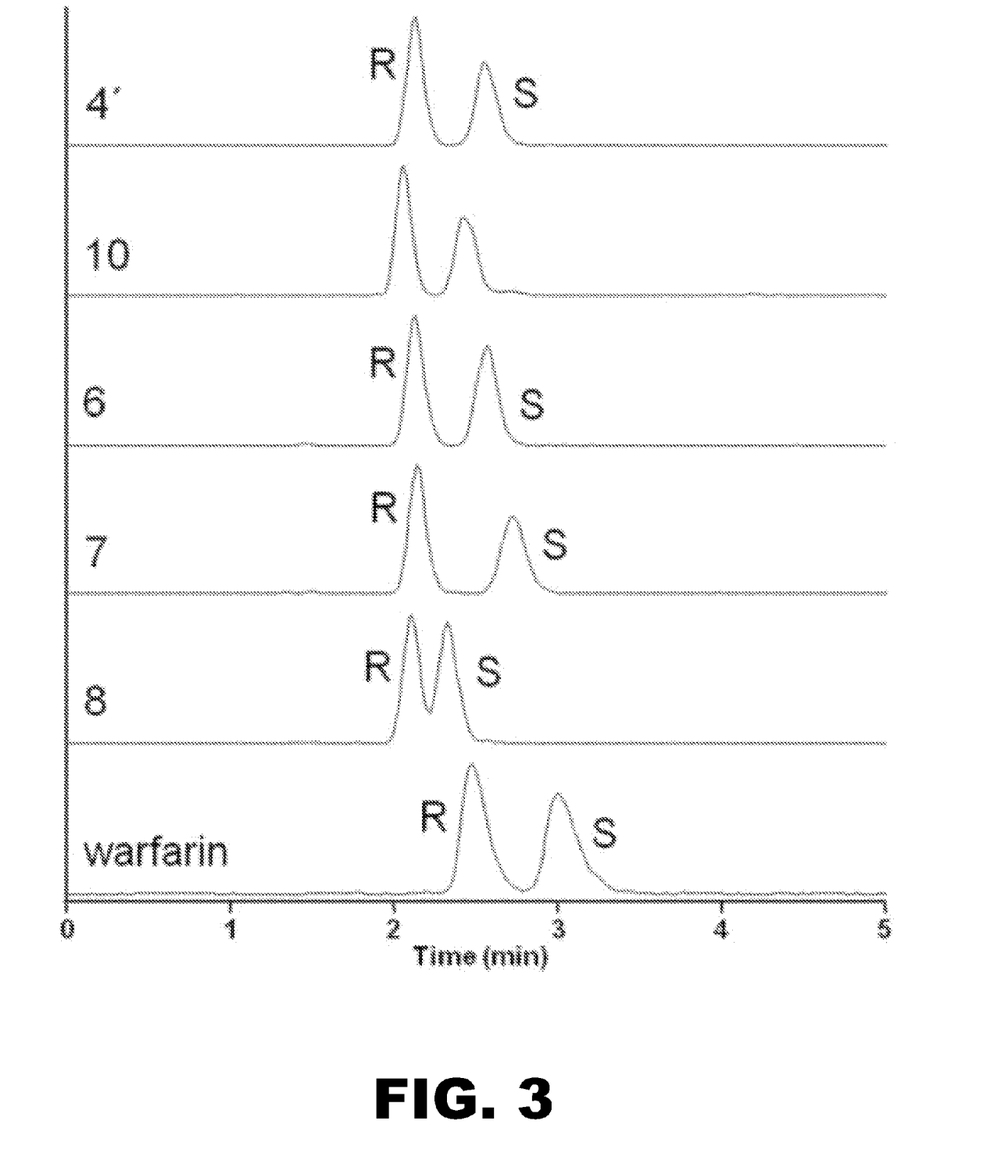
FIG. 3 illustrates that racemic standards (100 nM) of each hydroxywarfarin and warfarin were separated into their respective R and S enantiomers with the Chirobiotic V column. For each hydroxywarfarin, the R enantiomer eluted first followed by the S enantiomer. The method was isocratic with a flow rate of 300 μL/min and 45% methanol operating at room temperature (21.6-22.4° C.). Analytes were detected with MS/MS. Numbered chromatograms indicate sites of hydroxylation while R or S signifies stereochemistry e.g. 7=7-hydroxywarfarin. 10-Hydroxywarfarin contains a mixture of 4 isomers which were not fully resolved by the chiral column alone, but were separated with the dual phase method.

The separation of each hydroxywarfarin into its R and S enantiomeric components was investigated under a range of isocratic conditions using the same mobile phases and flow rates as with the phenyl column. The best separation of enantiomers was achieved with 20% methanol, but was maintained up to ~50% methanol. At room temperature (21.6-22.4° C.), each hydroxywarfarin achieved baseline separation into its respective R and S enantiomers with methanol compositions from 45% and below with the exception of 8-hydroxywarfarin which was partially separated at 45% methanol (FIG. 3). Higher column temperatures decreased the separation efficiency of hydroxywarfarin enantiomers. The composition of methanol needed to be approximately 20% to achieve maximum baseline separation for 8-hydroxywarfarin. Unfortunately, lower methanol compositions also led to increased retention times and broader peaks. At 45% methanol, all R-enantiomers had a retention time of approximately 2.1 minutes while S-enantiomers eluted between 2.3-2.8 minutes (FIG. 3). The operating pressure under these conditions was ~1500 psi. Therefore, sufficient separation on both phases is achieved with 45% methanol enabling in-series combination of both chromatographic systems.

Dual Phase Method Development.

The chromatography of the phenyl and chirobiotic V columns was characterized with identical mobile phases so that the two columns could be incorporated in-series with no additional pumps or switching mechanisms. Each column had a wide range of acceptable percent methanol compositions when operated individually, but, the only common range of isocratic operating conditions between them was approximately between 40 and 50% methanol. Even at high methanol compositions the phenyl column efficiently separated hydroxywarfarins. On the other hand, the chiral column required low percent methanol compositions to achieve chiral separation. At a composition of 45% methanol, each column achieved sufficient separation with acceptable run times when operated individually. The accompanying flow rate was 300 μL/min. The effect of temperature on separation was another critical factor for successful implementation for the dual-phase chromatography. The phenyl column performed optimally at 60° C. while the chiral column performed best at room temperature as opposed to elevated temperatures.

When the columns were operated in-series, separation of the hydroxywarfarin mixture into individual enantiomers was achieved (FIG. 2, bottom). The retention time for each hydroxywarfarin enantiomer was approximately equal to the sum of the retention times during characterization of the two columns individually. Each hydroxywarfarin separated into pairs of R and S enantiomers in the same order of elution from the phenyl column (FIG. 2, bottom). The operating pressure with both columns in-series was ~10,000 psi, which was equal to the sum of the operating pressure of each column individually. However, R- and S-8-hydroxywarfarin did not achieve baseline separation under these conditions, but did show distinct peaks.

The most challenging issue in combining the two columns in-series was achieving enough separation on the first column (phenyl) to enable additional enantiomeric separation between the metabolites on the second column (chirobiotic V). Further, peak widths from the first column had to be narrow enough to enable loading onto the second column. Previous attempts at implementing this approach using traditional HPLC columns (≥3.5 µm particles) and HPLC systems were unsuccessful (data not shown). The in-series combination of a traditional HPLC column (C18) with a chiral column generated too much back-pressure at the required flow rates. Further, peaks from a traditional column were too broad to enable loading onto the chiral column. The recent development of HPLC and the highly selective chemistry of the HPLC phenyl column are key technological advancements enabling dual-phase chromatography.

On the first column of novel dual phase HPLC-MS/MS method, the hydroxywarfarin peak widths were approximately 24 sec wide at the base and individual hydroxywarfarins were separated by more than 1 min (FIG. 2). This provided sufficient time for an additional chiral separation without interfering with neighboring peaks of the same SRM transition. Therefore, the success of dual-phase chromatography depended on a high efficient HPLC separation in the first phase. For the second phase, a traditional HPLC column was necessary because, no chiral HPLC columns are currently available. However, if chiral HPLC columns become available, it may be possible to enhance separation of hydroxywarfarins, simplify the experimental set-up, and achieve shorter run times as long as the increase in pressure can be managed.

Identification of Regio- and Stereo-Chemistry.

Figure 5:
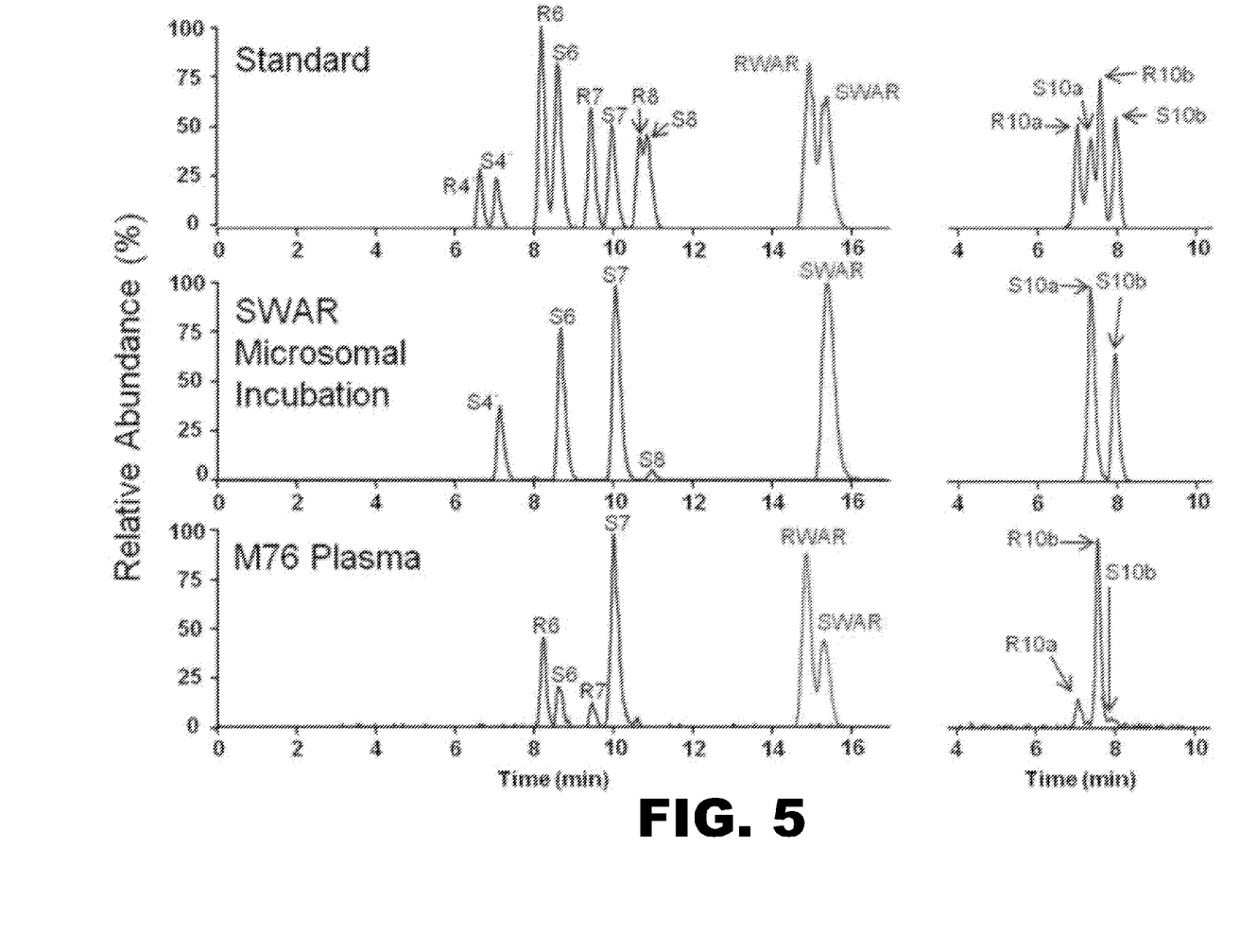
FIG. 5 depicts representative chromatograms of 100 nM racemic standards (top), enantiomerically pure 5-warfarin and S-hydroxywarfarins obtained from a reaction with pooled human liver microsomes (middle) and human plasma from a patient receiving warfarin (bottom). Numbers indicate sites of hydroxylation while R or S signifies stereochemistry e.g. S7=S-7-hydroxywarfarin. For clarity, 10-hydroxywarfarin tracings are shown separately.
Figure 7:
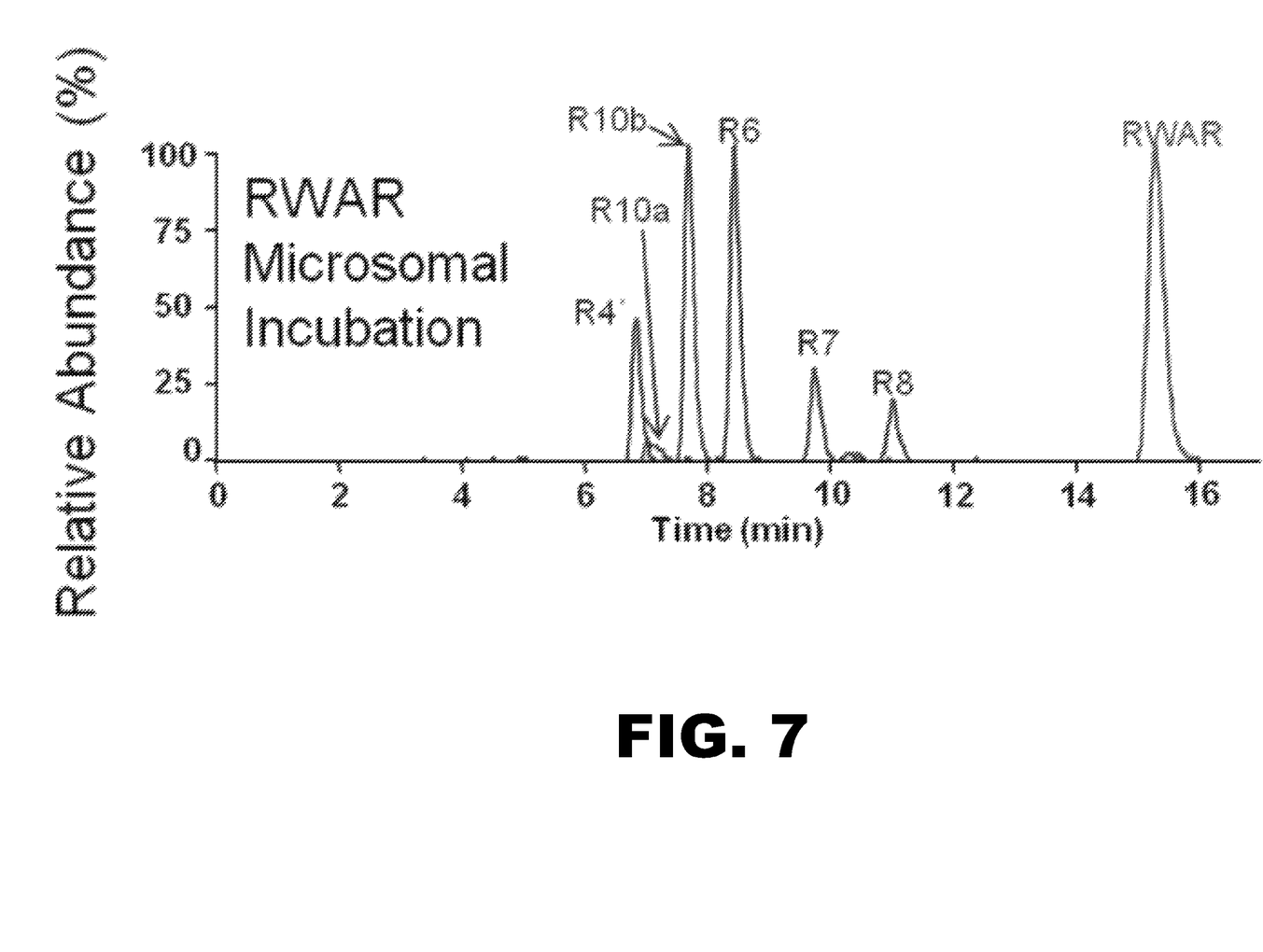
FIG. 7 presents representative chromatograms of enantiomerically pure R-warfarin and R-hydroxywarfarins obtained from a reaction with pooled human liver microsomes. Numbers indicate sites of hydroxylation while R or S signifies stereochemistry e.g. S7=S-7-hydroxywarfarin.

To confirm the stereochemistry for analytes in the dual-phase method, a mixture of warfarin metabolites obtained was analyzed by reacting pooled human liver microsomes with R- and S-warfarin, which generated enantiospecific hydroxywarfarin metabolites. The assignment of regio-chemistry was confirmed by injecting individual racemic hydroxywarfarin standards. The hydroxylated microsomal products of S-warfarin, matched the second peak in each pair of hydroxywarfarins as observed with commercially obtained standards (FIG. 5, middle). The hydroxywarfarin products obtained from reaction with R-warfarin matched the first peak in each pair of hydroxywarfarins (FIG. 7).

Figure 1:
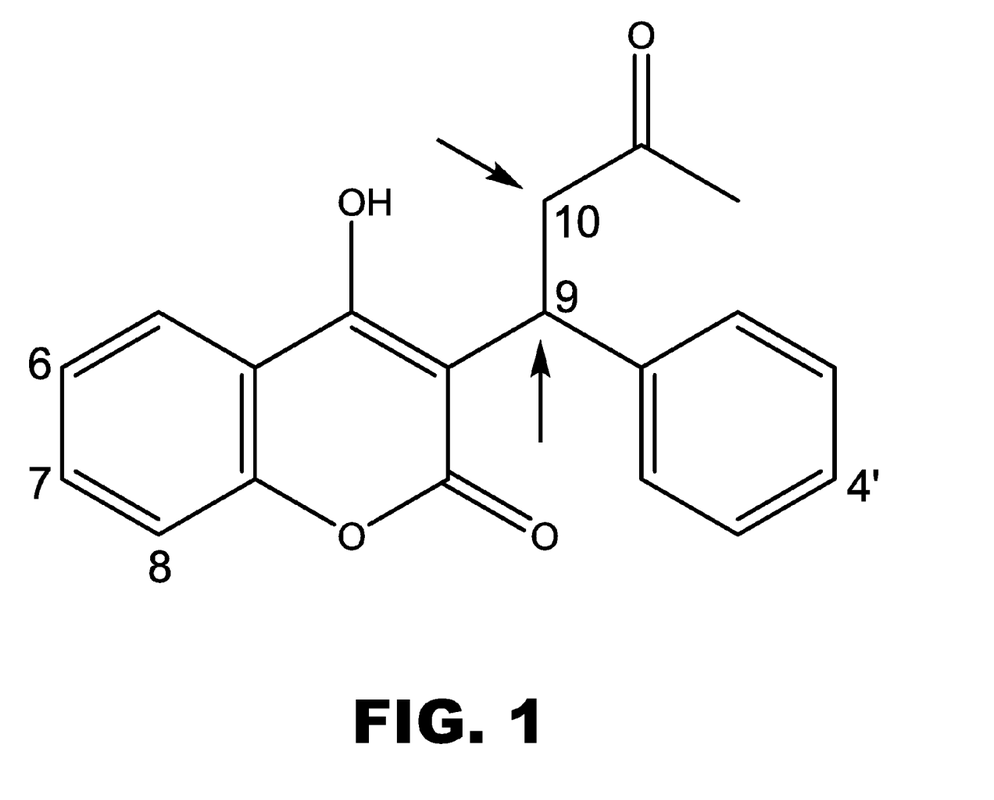
FIG. 1 illustrates the sites of warfarin hydroxylation by cytochrome P450s (carbons 4', 10, 6, 7, 8) and stereo-centers (arrows). Hydroxylation at position 10 introduces a second stereo-center, allowing for four possible isomers (RR, RS, SR, SS).
Figure 8:
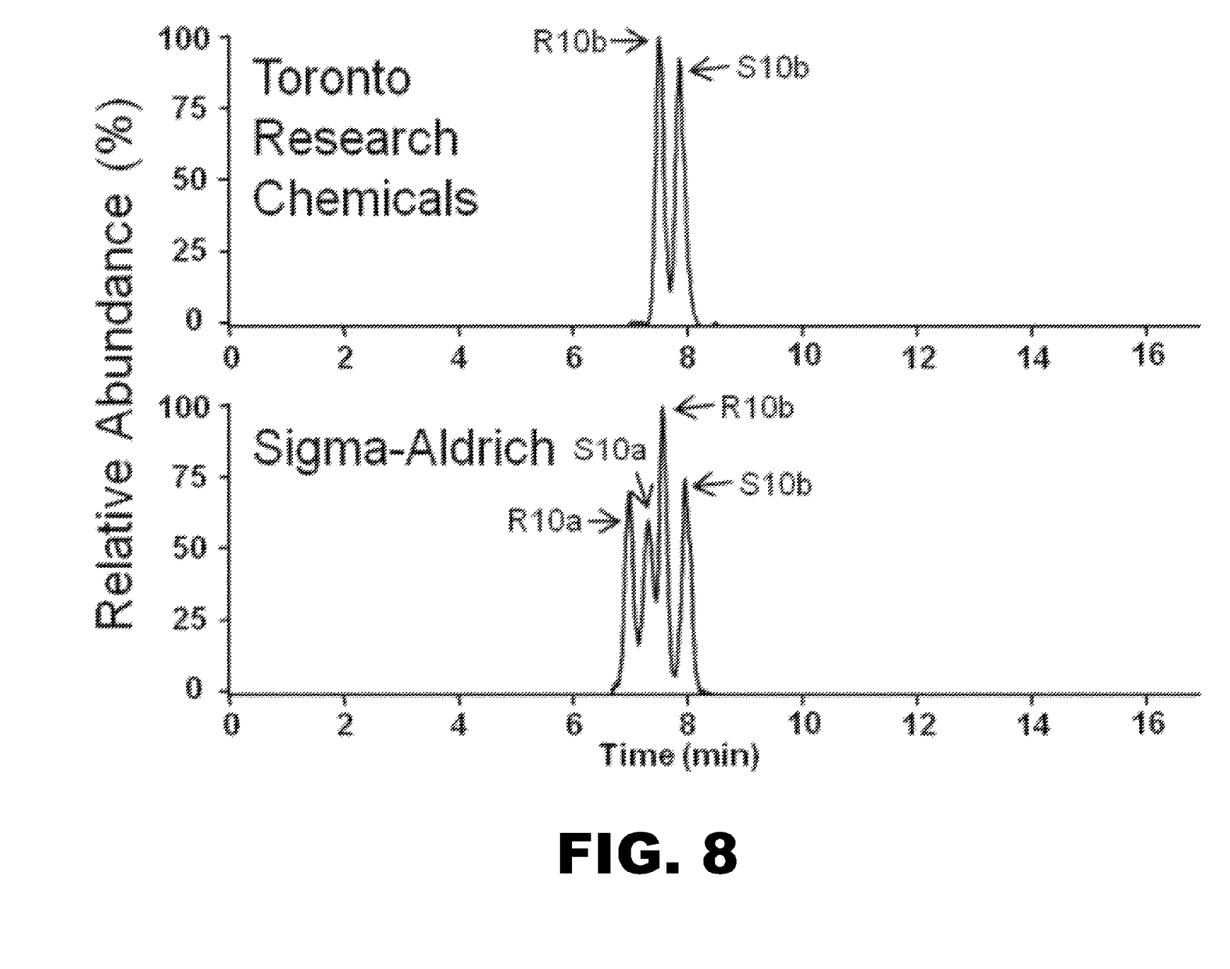
FIG. 8 shows representative chromatograms of commercial 10-hydroxywarfarin standards (100 nM) obtained from Toronto Research Chemicals (top) or Sigma-Aldrich (bottom). Samples were acquired with the dual-phase method. 10-Hydroxywarfarin contains two stereocenters such that four configurations are possible (RR, RS, SR, SS). However, only stereochemistry at carbon 9 could be assigned, therefore peaks were given an "a" or "b" designation based on elution order e.g. R10a=10-hydroxywarfarin with R stereochemistry at carbon 9 and unknown stereochemistry at carbon 10.

Historically, only R and S-10-hydroxywarfarin have been reported as possible metabolites. However, there are four isomeric forms of 10-hydroxywarfarin, because hydroxylation at the 10 position introduces a second chiral center. This fact has previously received much less to no attention in the literature and commercially available 10-hydroxywarfarin is simply labeled (R/S) instead of including all four configurations. Moreover, the isomeric composition of commercial standards varied between vendors making it impossible to assign the stereochemistry for the chiral center at carbon 10 on 10-hydroxywarfarin (FIG. 1). The present dual-phase HPLC-MS/MS method resolves all four of 10-hydroxywarfarin isomers and suggests that 10-hydroxywarfarin from Sigma-Aldrich contains an equal amount of all four isomers while 10-hydroxywarfarin from Toronto Research Chemicals contained only two of the isomers (FIG. 8). In the absence of standards, we were not able to identify which peaks represented R and S stereochemistry at position 10 and therefore labeled the individual pairs of R and 5-10-hydroxywarfarin enantiomers as 10Ra, 10Rb and 10Sa, 10Sb, respectively.

Figure 4:
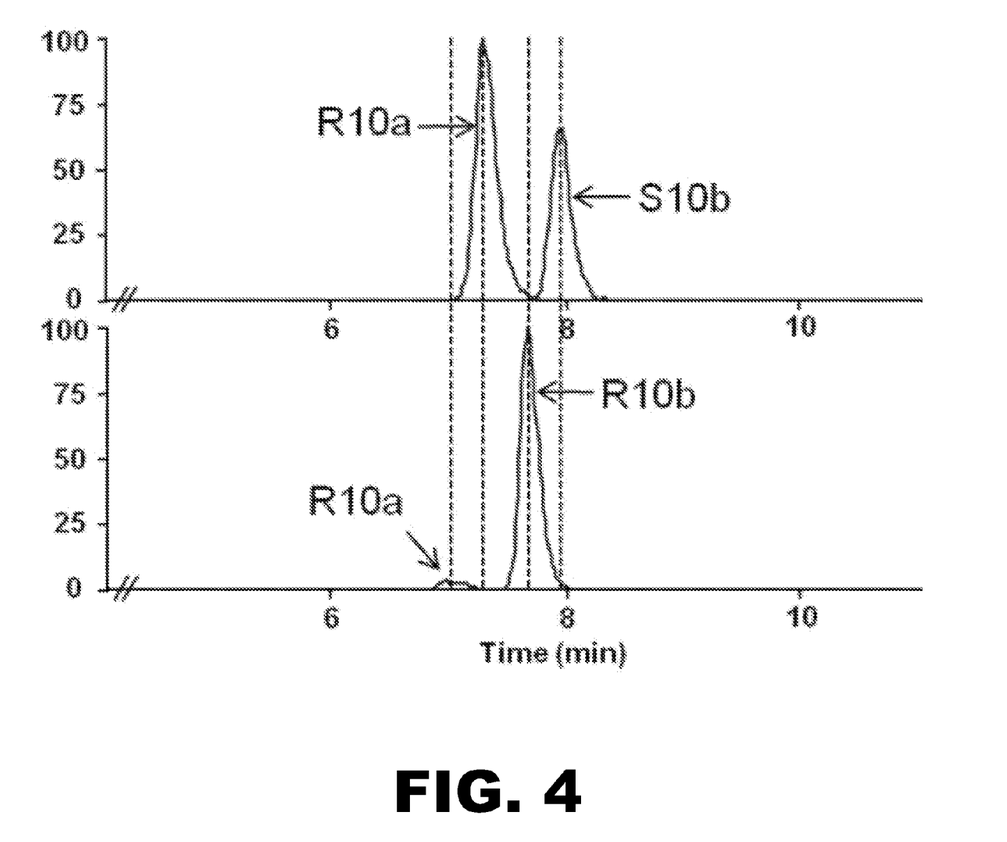
FIG. 4 shows that all four isomers of 10-hydroxywarfarin were generated from reactions of pooled human liver microsomes with either R-warfarin (top) or 5-warfarin (bottom). For each enantiomer of warfarin, two product peaks were observed, reflecting R or S stereochemistry about the 10 position. Due to the inability to assign stereochemistry, the sequential elution of these isomers are indicated by "a" or "b".

The microsomal incubations with R and S-warfarin clearly demonstrate the formation of all four 10-hydroxywarfarin isomers by human liver microsomes (FIG. 4). Incubations with R-warfarin (FIG. 7) produced two product peaks with the 10-hydroxywarfarin specific SRM as observed at 7.06 and 7.74 min at a ratio of 1:10 (25 µM reaction) or 1:18 (500 µM reaction). The presence of two peaks confirms the addition of a second chiral center of 10-hydroxywarfarin (FIG. 4). Similarly, two 10-hydroxywarfarin product peaks were observed for incubations with S-warfarin, eluting at 7.37 and 8.03 min at a 1.7:1 (25 µM reaction) or 1.6:1 (500 µM reaction) ratio. These two peaks further confirm the presence of a second chiral center on 10-hydroxywarfarin. For biomonitoring purposes we therefore assigned the 1st and 3rd peaks as 10-hydroxywarfarin metabolites derived from R-warfarin and the 2nd and 4th peaks as 10-hydroxywarfarin derived from S-warfarin. This appears to be the first report of separation and quantitation of all four 10-hydroxywarfarin isomers.

Assay Linearity and Limits of Detection and Quantification.

Figure 6:
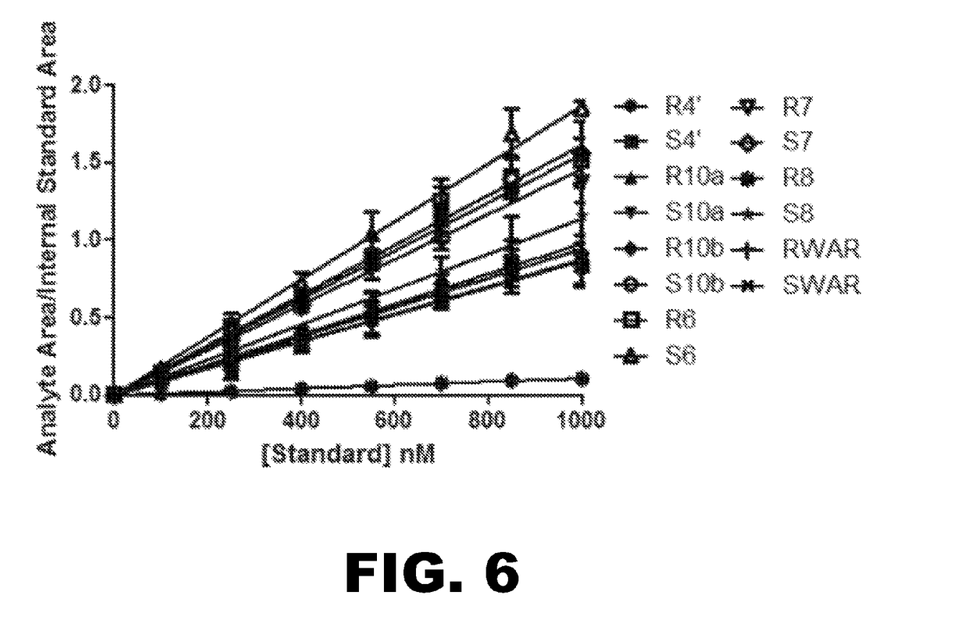
FIG. 6 shows the standard curves for each analyte ranging from 0 to 1000 nM. The concentration of each standard was plotted against the response ratio, the area of each analyte to the internal standard.

Standard curves containing all hydroxywarfarins and deuterated internal standards were prepared in potassium phosphate (50 mM, pH 7.4) and analyzed in triplicate with the assay conditions described above. Standards ranged from 0 nM to 1000 nM, and were linear with r2 values ≥0.97 (FIG. 6). The limit of detection (LOD) was approximately 10 femtomoles on column with a signal to noise of 10. This allows detection as low as 2 nM in plasma using a 5 µL injection of extracted plasma. The limit of quantification (LOQ) was defined as 5 times the LOD. Metabolite concentrations calculated to be below the limit of quantification were reported as LOQ.

Quantification of Plasma Profiles and Analysis of Inter-Day Variation.

The study was then expanded to the analysis of plasma samples from patients receiving warfarin to demonstrate suitability of the method for in vivo biomonitoring. All samples were from males aged 61, 75, 76, and 80 and are referred to as M61, M75, M75, and M80, respectively. Plasma samples were extracted as described above, and analyzed independently on three separate days. FIG. 5 (bottom) shows a representative plasma chromatogram and Table 1 shows the metabolite profiles for the four plasma samples. The coefficient of variation for analytes ranged from 0.2-6.2% (Table 1) representing the inter-day variation of the method. The ratio of R to 5-warfarin ranged from 1.6 to 2.4 among the plasma samples.

TABLE 1

Concentration of Plasma Hydroxywarfarins Across Three Independent Analyses
Concentration (nM)

|  | R4' | S4' | R10a | R10b | S10a | S10b | R6 | S6 | R7 | S7 | R8 | S8 | RWAR | SWAR |
|---|---|---|---|---|---|---|---|---|---|---|---|---|---|---|
| M61 | LOQ | LOQ | 55 (5.6) | 273 (3.7) | LOQ | 27 (3.4) | 57 (1.6) | 44 (4.7) | 37 (2.2) | 452 (3.2) | — | — | 3865 (2.3) | 1722 (4.1) |
| M75 | — | LOQ | 52 (2.4) | 297 (4.7) | LOQ | 26 (0.2) | 98 (1.9) | 47 (2.3) | 50 (3.5) | 343 (3.6) | — | — | 4833 (1.80) | 2705 (6.2) |
| M76 | LOQ | LOQ | 36 (1.4) | 177 (2.8) | — | 16 (3.5) | 92 (4.9) | 51 (1.9) | 36 (4.2) | 545 (0.8) | — | — | 4811 (2.3) | 3460 (2.7) |

TABLE 1-continued

Concentration of Plasma Hydroxywarfarins Across Three Independent Analyses
Concentration (nM)

| | R4' | S4' | R10a | R10b | S10a | S10b | R6 | S6 | R7 | S7 | R8 | S8 | RWAR | SWAR |
|---|---|---|---|---|---|---|---|---|---|---|---|---|---|---|
| M80 | — | — | 13 (5.0) | 82 (4.5) | — | 13 (4.0) | 31 (4.7) | 13 (3.6) | 9 (6.0) | 188 (4.1) | — | — | 1437 (2.7) | 689 (2.8) |

( ) = Coefficient of variation (%)
LOQ = lower than limit of quantitation
— = lower than limit of detection For these patients, the major observed metabolites were R-10-hydroxywarfarins (R10a and R10b) and S-7-hydroxywarfarin indicating the importance of CYP3A and CYP2C9, respectively, in warfarin metabolism. This appears to be the first demonstration of the formation of all four 10-hydroxywarfarin isomers in humans. Three of the 10-hydroxywarfarin isomers were clearly shown to be present in human plasma, (FIG. 5, bottom and Table 1), while one isomer (S10a) was detected but below the limit of quantitation. Together with the microsomal data there is strong evidence for the formation of all four 10-hydroxywarfarin isomers in humans. Future studies will be needed to determine the biological significance of the individual 10-hydroxywarfarin isomers. The total plasma concentration of 10-hydroxywarfarin derived from both R and S-warfarin was higher than S-7-hydroxywarfarin concentrations in M61 and M75. For patients M76 and M80, S-7-hydroxywarfarin was the most abundant metabolite. In addition, R-7-hydroxywarfarin was observed in all four plasma samples, while 4"-hydroxywarfarin was observed in some samples, but was below the limit of quantitation. In these samples, 8-hydroxywarfarin was below the limit of detection.

(c) Conclusions

A dual phase HPLC method was developed and validated for profiling of specific region- and enantio-specific hydroxywarfarins and warfarin. The method provides excellent chromatographic separation of warfarin and hydroxywarfarins in 17 minutes. Additionally, it was found that the columns could be connected in-series with either column being the first column.

The analysis of patient samples demonstrated the potential of the method to accurately quantify warfarin and its metabolites present in human plasma with high sensitivity. The dual phase method marks a significant advancement in the profiling of chiral warfarin and its hydroxylated metabolites. Prior studies have been limited to analyzing either warfarin enantiomers or racemic forms of hydroxywarfarin metabolites. Through the novel dual phase HPLC method, it is now possible to effectively assess the widest array of warfarin metabolites for identifying and validating potential biomarkers to metabolic pathways and surrogate markers corresponding to patient responses to warfarin therapy.

What is claimed is:

1. A chromatography column containing at least one chiral stationary phase and at least one achiral stationary phase, wherein each stationary phase is affixed to a plurality of particles.

2. The chromatography column of claim 1, wherein each chiral stationary phase comprises a chiral selector chosen from a macrocyclic glycopeptide, a cyclodextrin, a polysaccharide polymer, a small molecule, and a protein.

3. The chromatography column of claim 1, wherein each achiral stationary phase comprises a functional group chosen from alkyl, alkenyl, alkynyl, aryl, alkylaryl, alkylamide, alkylamino, alkyldiol, alkylcarboxy, alkylsulfonic, amide, amine, cyano, diol, carboxy, and sulfonic.

4. The chromatography column of claim 1, wherein each plurality of particles has an average particle diameter from about 0.5 micron to about 15 microns and an average pore size from about 25 angstroms to about 500 angstroms.

5. The chromatography column of claim 1, wherein the chromatography column comprises at least two discrete zones, each zone comprising one of the stationary phases.

6. The chromatography column of claim 1, wherein the chromatography column comprises a heterogeneous mixture of the stationary phases.

7. The chromatography column of claim 1, wherein the chromatography column is used in a technique chosen from high performance liquid chromatography, ultra high performance liquid chromatography, supercritical fluid chromatography, simulated moving bed chromatography, gas chromatography, ion chromatography, counter current liquid chromatography, capillary electrophoresis, and capillary electrochromatography.

8. The chromatography column of claim 1, wherein the chromatography column comprises one chiral stationary phase and one achiral stationary phase.

9. A method for enantioseparating at least one chiral molecule, the method comprising contacting a mixture comprising one or more chiral molecules with the chromatography column of claim 1 such that enantiomers of the chiral molecules are separated.

* * * * *